United States Patent [19]

Shida et al.

[11] Patent Number: 5,094,684
[45] Date of Patent: * Mar. 10, 1992

[54] DERIVATIVE OF 1,5-DIPHENYL-1H-1,2-TRIAZOLE-3-CARBOXAMIDE, HERBICIDAL COMPOSITIONS CONTAINING THE DERIVATIVE AND PROCESS FOR PRODUCING THE DERIVATIVE

[75] Inventors: Takafumi Shida; Hideo Arabori; Takeo Watanabe; Shiro Yamazaki; Hiroyasu Shinkawa, all of Iwaki, Japan

[73] Assignee: Kureha Kagaku Kogyo Kabushiki Kaisha, Tokyo, Japan

[ * ] Notice: The portion of the term of this patent subsequent to Nov. 27, 2007 has been disclaimed.

[21] Appl. No.: 554,986

[22] Filed: Jul. 17, 1990

Related U.S. Application Data

[63] Continuation of Ser. No. 202,628, Jun. 6, 1988, abandoned.

[30] Foreign Application Priority Data

Jun. 8, 1987 [JP] Japan .................. 62-143020

[51] Int. Cl.$^5$ .................. A01N 43/653; C07D 249/14
[52] U.S. Cl. .................. 71/92; 548/266.8
[58] Field of Search .................. 71/92; 548/266.8

[56] References Cited

U.S. PATENT DOCUMENTS

| | | | |
|---|---|---|---|
| 4,269,845 | 5/1981 | Worthington et al. | 424/269 |
| 4,492,597 | 1/1985 | Aoki et al. | 71/92 |
| 4,717,734 | 1/1988 | Rogers et al. | 514/359 |
| 4,820,334 | 4/1989 | Shida et al. | 548/262 |
| 4,919,707 | 4/1990 | Shida et al. | 548/266.8 |

FOREIGN PATENT DOCUMENTS

| | | |
|---|---|---|
| 0070089 | 6/1983 | European Pat. Off. . |
| 0189300 | 7/1986 | European Pat. Off. . |
| 0220956 | 5/1987 | European Pat. Off. . |
| 58-185572 | 10/1983 | Japan . |
| 59-98004 | 6/1984 | Japan . |
| 2120665 | 12/1983 | United Kingdom . |

OTHER PUBLICATIONS

Chemical Abstracts, vol. 100, No. 19, May 7, 1984, p. 536, Abstract 156607x.

*Primary Examiner*—Richard L. Raymond
*Assistant Examiner*—Peter G. O'Sullivan
*Attorney, Agent, or Firm*—Nixon & Vanderhye

[57] ABSTRACT

Disclosed herein is a derivative of 1,5-diphenyl-1H-1,2,4-triazole-3-carboxamide represented by the following formula (I):

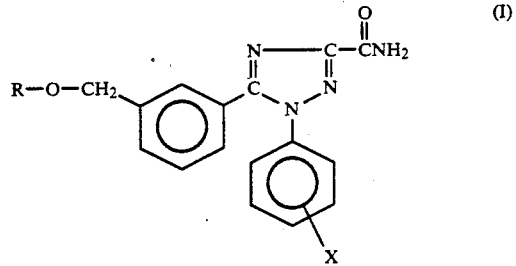

wherein R represents an alkyl group of 2 to 10 carbon atoms, which is substituted by fluorine atom(s), and X represents a hydrogen atom or a fluorine atom, a process for producing the derivative and herbicidal compositions containing the derivative of 1,5-diphenyl-1H-1,2,4-triazole-3-carboxamide as an active ingredient.

6 Claims, No Drawings

DERIVATIVE OF 1,5-DIPHENYL-1H-1,2-TRIAZOLE-3-CARBOXAMIDE, HERBICIDAL COMPOSITIONS CONTAINING THE DERIVATIVE AND PROCESS FOR PRODUCING THE DERIVATIVE

This is a continuation of application Ser. No. 202,628, filed June 6, 1988, now abandoned.

BACKGROUND OF THE INVENTION

The present invention relates to a derivative of 1,5-diphenyl-1H-1,2,4-triazole-3-carboxamide, which are utilized as an active ingredient of herbicidal compositions, a process for producing the derivative and a herbicidal composition containing the derivative as a active ingredient. More in detail, the present invention relates to the derivative of 1,5-diphenyl-1H-1,2,4-triazole-3-carboxamide represented by the following formula (I):

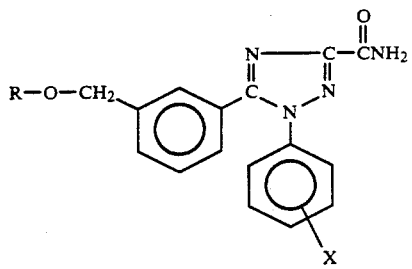

wherein R represents an alkyl group of 2 to 10 carbon atoms, which is substituted by fluorine atom(s), and X represents a hydrogen atom or a fluorine atom, a process for producing the derivative and a herbicidal composition containing the derivative of 1,5-diphenyl-1H-1,2,4-triazole-3-carboxamide as an active ingredient.

Rice plant, wheat, corn, etc. are important crops and the use of herbicide is indispensable for contriving the increased yield of these crops by protecting the crops from the damage due to weed plants.

That the derivatives of 1,5-diphenyl-1H-1,2,4-triazole-3-carboxamide have the herbicidal function has been hitherto described in Japanese Patent Applications Laid-Open (KOKAI) Nos. 57-193406(1982), 58-185572(1983) and 59-98004(1984).

For instance, Japanese Patent Application Laid-Open (KOKAI) No. 57-193406(1982)(corresponding to U.S. Pat. No. 4,492,597) discloses a herbicidal composition containing as an active ingredient a derivative of 1,2,4-triazole represented by the formula:

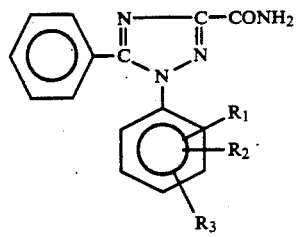

wherein $R_1$ is a hydrogen atom, a fluorine atom, a chlorine atom, an iodine atom, a lower alkyl group having 1 to 3 carbon atoms, an alkyl group substituted with a fluorine atom, a nitro group or a methoxy group; $R_2$ is a hydrogen atom, a chlorine atom or a methyl group; and $R_3$ is a hydrogen atom or a methyl group.

In Japanese Patent Application Laid-Open (KOKAI) No. 59-98004(1984), disclosed is a herbicidal composition containing a derivative of 1,2,4-triazole represented by the formula:

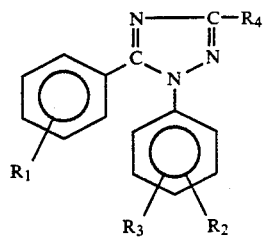

wherein $R_1$ and $R_2$ represent independently a hydrogen atom, a halogen atom, an alkyl group or a halogenoalkyl group; $R_3$ is a hydrogen atom, a halogen atom or an alkyl group; and $R_4$ is a cyano group, carbamoyl group, thiocarbamoyl group, N-alkylcarbamoyl group, N-halogenoalkylcarbamoyl group, N-methoxyalkylcarbamoyl group, N-alkenylcarbamoyl group, N-halogenoalkenylcarbamoyl group, N-acylcarbamoyl group, N-halogenoacylcarbamoyl group or N-methylthiocarbamoylcarbamoyl group.

Also, Japanese Patent Application Laid-Open (KOKAI) No. 58-185572(1983) discloses a derivative of 1,2,4-triazole represented by the formula:

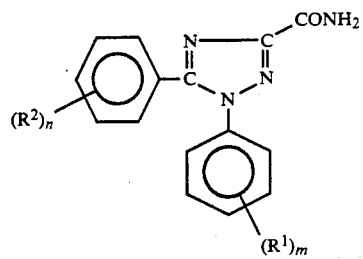

wherein $R^1$ represents a hydrogen atom or an alkyl group; m represents 0, 1 or 2; $R^2$ represents an alkyl group, an alkoxyl group, a nitro group or a halogen atom; and n represents 1 or 2.

Further, the herbicide containing a derivative of 1,2,4-triazole has been proposed also in the following patents and patent applications.

U.K. Patent No. 2,120,665 discloses a herbicidal composition comprising a derivative of 1,2,4-triazole represented by the general formula:

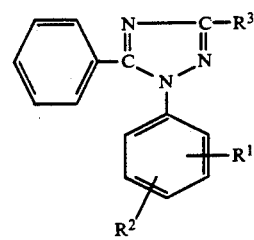

wherein $R^1$ represents a hydrogen atom, a halogen atom or a $(C_1-C_2)$ alkyl group; $R^2$ represents a hydrogen atom, a halogen atom, a $(C_1-C_2)$ alkyl group, a halogeno $(C_1-C_2)$ alkyl group, a methoxy group, a cyano group, a methoxymethyl group, a methylthio group, a methoxycarbonyl group or an isopropoxycarbonyl group; and $R^3$ represents a thioamide group or a group represented by the general formula:

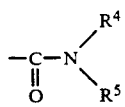

wherein $R^4$ represents a hydrogen atom, a $(C_1-C_2)$ alkyl group or a hydroxy $(C_1-C_2)$ alkyl group and $R^5$ represents a hydrogen atom, a $(C_1-C_2)$ alkyl group, a halogeno $(C_1-C_2)$ alkyl group, a hydroxy $(C_1-C_2)$ alkyl group, a cyanomethyl group, an acetyl group, a halogenoacetyl group, a methoxyacetyl group, an amino group, a phenyl group, a methoxy group, a hydroxyl group, a $(C_2-C_3)$ alkenyl group, a halogeno $(C_2-C_3)$ alkenyl group, an isopropylcarbonyl group, a methylthiocarbonyl group or a 2-methoxyethyl group and a herbicidally acceptable carrier or diluent thereof.

European Patent No. 0,220,956 discloses a herbicidal composition comprising a 1,2,4-triazole-3-carboxamide compound represented by the formula:

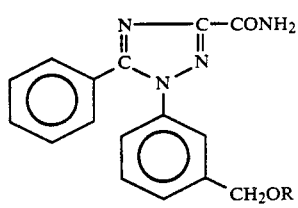

wherein R represents a straight-chain or branched-chain saturated $(C_2-C_{10})$ alkyl group which is unsubstituted or substituted by fluorine atom(s); a cyclic saturated $(C_3-C_{10})$ alkyl group which is unsubstituted or substituted by fluorine atom(s); a straight-chain, branched-chain or cyclic unsaturated $(C_3-C_{10})$ alkyl group which is unsubstituted or substituted by fluorine atom(s); a group represented by the formula:

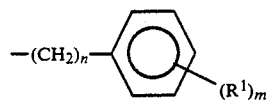

wherein $R^1$ represents a halogen atom, a $(C_1-C_3)$alkyl group, a $(C_1-C_3)$alkoxy group or a fluorine-substituted $(C_1-C_3)$alkyl group, m is 0 or an integer of from 1 to 5 and n is 0 or 1; a straight-chain or branched-chain saturated $(C_1-C_8)$alkoxy$(C_2-C_{10})$alkyl group; a straight-chain or branched-chain unsaturated $(C_1-C_8)$alkoxy $(C_2-C_{10})$alkyl group; a phenoxy$(C_2-C_6)$alkyl group; an aralkoxy$(C_2-C_6)$alkyl group; a phenoxy$(C_2-C_6)$alkyl group having phenyl group(s) substituted by halogen atom(s) or $(C_1-C_3)$alkyl group(s); an aralkoxy$(C_2-C_6)$alkyl group having phenyl group(s) substituted by halogen atom(s) or $(C_1-C_3)$alkyl group(s); a $[(C_1-C_8)$alkoxy$(C_2-C_{10})$alkoxy] $(C_2-C_{10})$alkyl group; or a group represented by the formula:

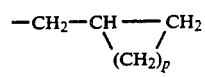

wherein p is an integer of from 1 to 8, and a herbicidally acceptable carrier or adjuvant.

In U.S. patent application No. 07/042,321, proposed is a herbicidal composition comprising a herbicidally effective amount of a derivative of 1,5-diphenyl-1H-1,2,4-triazole-3-carboxamide represented by the following formula as an active ingredient:

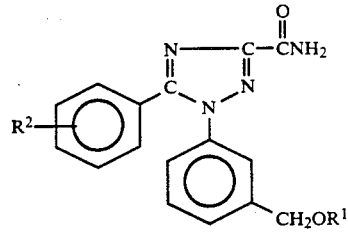

wherein $R^1$ represents a straight-chain alkyl group of 2 to 10 carbon atoms; a branched-chain alkyl group or cycloalkyl group of 3 to 10 carbon atoms; a (cycloalkyl)alkyl group of 4 to 10 carbon atoms; an unsubstituted or halogen-substituted phenyl group; an aralkyl group of 7 to 9 carbon atoms; an alkenyl group of 3 to 6 carbon atoms or an alkyl group of 2 to 10 carbon atoms, which has been substituted by 1 to 19 fluorine atoms, and $R^2$ represents a fluorine atom, a chlorine atom, a methyl group or a methoxy group, and a herbicidally acceptable carrier or adjuvant.

In U.S. patent application No. 07/162,699 filed Mar. 1, 1988 (corresponding to Japanese Patent Application No. 62-54579(1987) filed Mar. 10, 1987 and No. 62-153031(1987) filed June 19, 1987), proposed is a herbicidal composition comprising as an active ingredient a herbicidally effective amount of a derivative of 1,5-diphenyl-1H-1,2,4-triazole-3-carboxamide represented by the following formula:

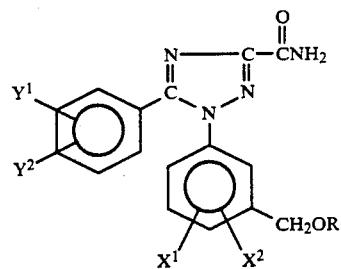

wherein R is a straight-chain alkyl group having 1 to 10 carbon atoms, which is an unsubstituted or substituted with 1 to 19 fluorine atoms; a branched alkyl group having 3 to 10 carbon atoms, which is an unsubstituted or substituted with 1 to 19 fluorine atoms; a cyclic alkyl group having 3 to 10 carbon atoms; an alkyl group having 1 to 3 carbon atoms which is substituted with an alicyclic structure having 3 to 7 carbon atoms; a phenyl group or an aralkyl group having 7 to 9 carbon atoms; $X^1$ is a halogen atom or an alkyl group having 1 to 3 carbon atoms; $X^2$ is a hydrogen atom, a halogen atom or an alkyl group having 1 to 3 carbon atoms; $Y^1$ is a hydrogen atom or a fluorine atom; and $Y^2$ is a hydrogen atom or a fluorine atom, and herbicidally acceptable carrier or adjuvant.

The development of a compound excellent in selectivity in which the compound shows an excellent herbicidal activity only to the weeds without injuring the useful crops such as rice plant, wheat, corn, etc. is strongly demanded.

As a result of the present inventors' studies for offering a compound showing an excellent herbicidal effect and at the same time, does not injuring to the useful crops such as rice plant, wheat, corn, etc., it has been found out that a derivative of 1,5-diphenyl-1H-1,2,4-triazole-3-carboxamide represented by the following formula (I) have the excellent herbicidal effect, and on the basis of this finding, the present invention has been attained.

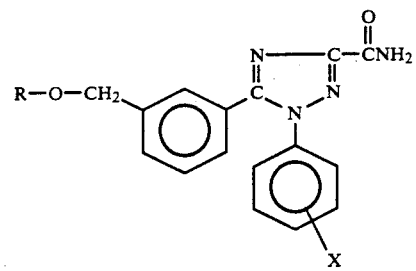

(I)

wherein R is an alkyl group of 2 to 10 carbon atoms, which is substituted by fluorine atom(s), and X represents a hydrogen atom or a fluorine atom.

The compound represented by the formula (I) is different from the compounds described in the aforementioned patents and patent applications in the point that the compound represented by the formula (I) has the group of —CH$_2$OR (wherein R represents the same meaning as above) at the 3-position of the phenyl group of the 5-position of 1,5-diphenyl-1H-1,2,4-triazole-3-carboxamide, and the compounds represented by the formula (I) are the novel compounds.

Namely, the object of the present invention is provided with a derivative of 1,5-diphenyl-1H-1,2,4-triazole-3-carboxamide which have the selectively herbicidal activity in which the derivative shows the excellent herbicidal function to the gramineous weeds and broad-leaved plants, particularly to the broad-leaved plants and on the other hand, does not shows any phytotoxicity to the crops such as rice plant, wheat, corn, etc. and the herbicidal composition containing the derivative thereof as an active ingredient.

SUMMARY OF THE INVENTION

In a first aspect of the present invention, there is provided a derivative of 1,5-diphenyl-1H-1,2,4-triazole-3-carboxamide represented by the formula (I):

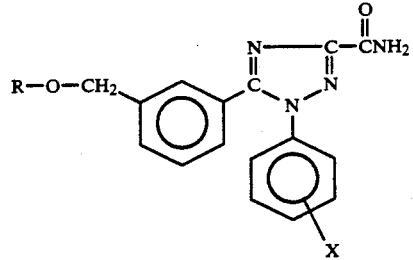

(I)

wherein R represents an alkyl group of 2 to 10 carbon atoms, which is substituted by fluorine atom(s), and X represents a hydrogen atom or a fluorine atom.

In a second aspect of the present invention, there is provided a process for producing a derivative of 1,5-diphenyl-1H-1,2,4-triazole-3-carboxamide represented by the formula (I):

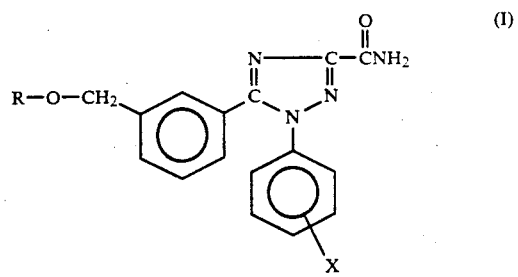

(I)

wherein R represents an alkyl group of 2 to 10 carbon atoms, which is substituted by fluorine atom(s) and X represents a hydrogen atom or a fluorine atom, which the process comprises the steps of reacting ammonia with a derivative of 2-phenyl-4-phenylhydrazono-2-oxazolin-5-one represented by the formula (II):

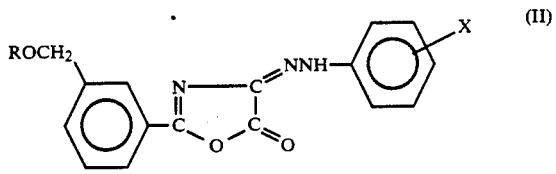

(II)

wherein R represents an alkyl group of 2 to 10 carbon atoms, which is substituted by fluorine atom(s), and X represents a hydrogen atom or a fluorine atom, in an organic solvent at a temperature of −10° to 150° C., adding to the thus formed reaction mixture hydrochloric acid, acetic acid to make the reaction mixture acidic, and reacting the thus treated reaction mixture at a temperature of 0° to 150° C.

In a third aspect of the present invention, there is provided a herbicidal composition comprising as an active ingredient, a herbicidally effective amount of a derivative of 1,5-diphenyl-1H-1,2,4-triazole-3-carboxamide represented by the formula (I):

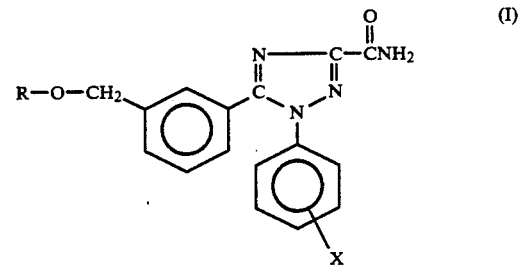

(I)

wherein R represents an alkyl group of 2 to 10 carbon atoms, which is substituted by fluorine atom(s), and X represents a hydrogen atom or a fluorine atom.

In a fourth aspect of the present invention, there is provided a derivative of 2-phenyl-4-phenylhydrazono-2-oxazolin-5-one represented by the formula (II):

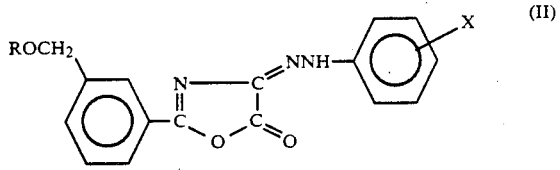

wherein R represents an alkyl group of 2 to 10 carbon atoms, which is substituted by fluorine atom(s), and X represents a hydrogen atom or a fluorine atom, as an intermediate of the derivative of 1,5-diphenyl-1H-1,2,4-triazole-3-carboxamide represented by the formula (I).

In a fifth aspect of the present invention, there is provided a process for producing a derivative of 2-phenyl-4-phenylhydrazono-2-oxazolin-5-one represented by the formula (II):

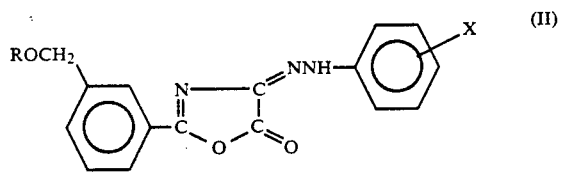

wherein R represents an alkyl group of 2 to 10 carbon atoms, which is substituted by fluorine atom(s), and X represents a hydrogen atom or a fluorine atom, which the process comprises i) reacting not less than one equivalent or RO⊖A⊕ (wherein A represents a sodium atom or a potassium atom and R represents an alkyl group of 2 to 10 carbon atoms, which is substituted by fluorine atom(s)), with 3-(chloromethyl) benzoyl chloride represented by the formula (III):

in an aprotic organic solvent, thereby obtaining alkoxymethylbenzoate represented by the formula (IV'):

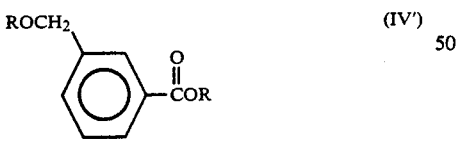

wherein R represents an alkyl group of 2 to 10 carbon atoms, which is substituted by fluorine atom(s); and ii) hydrolyzing the thus obtained alkoxymethylbenzoate represented by the formula (IV'), thereby obtaining alkoxymethylbenzoic acid represented by the formula (IV):

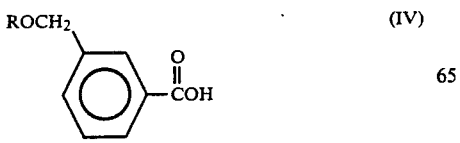

wherein R represents an alkyl group of 2 to 10 carbon atoms, which is substituted by fluorine atom(s);

iii) reacting the thus obtained alkoxymethylbenzoic acid represented by the formula (IV) with thionyl chloride, thereby obtaining alkoxymethylbenzoyl chloride represented by the formula (IV''):

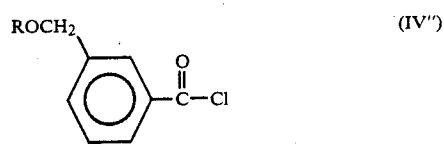

wherein R represents an alkyl group of 2 to 10 carbon atoms, which is substituted by fluorine atom(s);

iv) reacting the thus obtained alkoxymethylbenzoyl chloride represented by the formula (IV'') with glycine in the presence of an inorganic base at a temperature of $-10°$ to 15° C. in water or a mixed solvent of an aprotic solvent and water, thereby obtaining alkoxymethylhippuric acid represented by the formula (V):

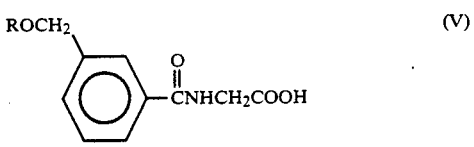

wherein R represents an alkyl group of 2 to 10 carbon atoms, which is substituted by fluorine atom(s);

v) reacting the thus obtained alkoxymethylhippuric acid represented by the formula (V) with acetic anhydride, thereby obtaining a derivative of 2-phenyl-2-oxazolin-5-one represented by the formula (VI):

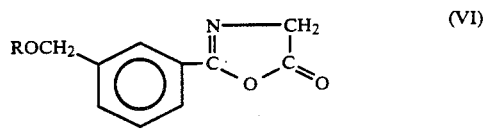

wherein R represents an alkyl group of 2 to 10 carbon atoms, which is substituted by fluorine atom(s); and vi) reacting the thus obtained derivative of 2-phenyl-2-oxazolin-5-one represented by the formula (VI) at a temperature of not higher than 60° C. with a diazonium salt represented by the following formula:

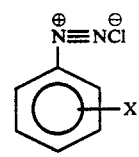

wherein X represents a hydrogen atom or a fluorine atom, which is obtained by reacting aniline represented by the following formula:

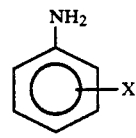

wherein X represents a hydrogen atom or a fluorine atom with sodium nitrite, thereby obtaining said derivative of 2-phenyl-4phenylhydrazono-2-oxazolin-5-one.

In a sixth aspect of the present invention, there is provided an alkoxymethylhippuric acid represented by the formula (V):

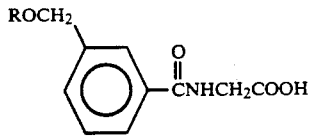
(V)

wherein R represents an alkyl group of 2 to 10 carbon atoms, which is substituted by fluorine atom(s), as an intermediate of the derivative of 1,5-diphenyl-1H-1,2,4-triazole-3-carboxamide represented by the formula (I).

In a seventh aspect of the present invention, there is provided a process for producing an alkoxymethylhippuric acid represented by the formula (V):

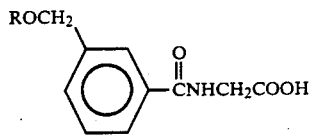
(V)

wherein R represents an alkyl group of 2 to 10 carbon atoms, which is substituted by fluorine atom(s), which the process comprises i) reacting not less than one equivalent of $R\ominus A\oplus$, (wherein A represents a sodium atom or a potassium atom and R represents an alkyl group of 2 to 10 carbon atoms, which is substituted by fluorine atom(s), with 3-(chloromethyl)benzoyl chloride represented by the formula (III):

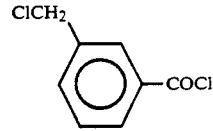
(III)

thereby obtaining an alkoxymethylbenzoate represented by the formula (IV'):

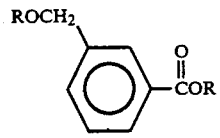
(IV')

wherein R represents an alkyl group of 2 to 10 carbon atoms, which is substituted by fluorine atom(s);

ii) hydrolyzing the thus obtained alkoxymethylbenzoate represented by the formula (IV'), thereby obtaining alkoxymethylbenzoic acid represented by the formula (IV):

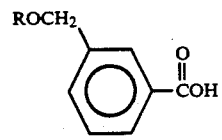
(IV)

wherein R represents an alkyl group of 2 to 10 carbon atoms, which is substituted by fluorine atom(s);

iii) reacting the thus obtained alkoxymethylbenzoic acid represented by the formula (IV) with thionyl chloride, thereby obtaining alkoxymethylbenzoyl chloride represented by the formula (IV"):

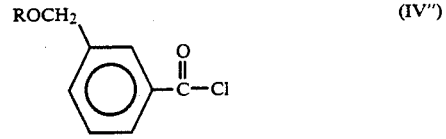
(IV")

wherein R represents an alkyl group of 2 to 10 carbon atoms, which is substituted by fluorine atom(s); and iv) reacting the thus obtained alkoxymethylbenzoyl chloride represented by the formula (IV") with glycine in the presence of an inorganic base at a temperature of $-10°$ to 15° C. in water or in a mixed solvent of an aprotic organic solvent and water, thereby obtaining alkoxymethylhippuric acid represented by the formula (V).

In an eighth aspect of the present invention, there is provided an alkoxymethylbenzoic acid represented by the formula (IV):

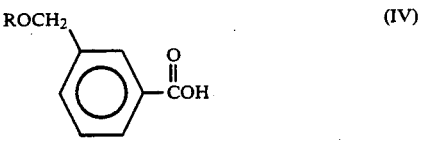
(IV)

wherein R represents an alkyl group of 2 to 10 carbon atoms, which is substituted by fluorine atom(s), as an intermediate of the derivative of 1,5-diphenyl-1H-1,2,4-triazole-3-carboxamide represented by the formula (I).

In a ninth aspect of the present invention, there is provided a process for producing an alkoxymethylbenzoic acid represented by the formula (IV):

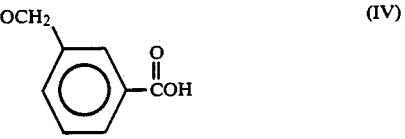
(IV)

wherein R represents an alkyl group of 2 to 10 carbon atoms, which is substituted by fluorine atom(s), which the process comprises i) reacting not less than one equivalent of $RO\ominus A\oplus$ (wherein A represents a sodium atom or a potassium atom and R represents an alkyl group of 2 to 10 carbon atoms, which is substituted by fluorine atom(s), with 3-(chloromethyl)benzoyl chloride represented by the formula (III):

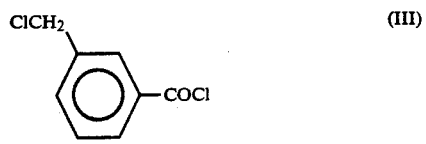
(III)

in an aprotic organic solvent, thereby obtaining an alkoxymethylbenzoate represented by the formula (IV'):

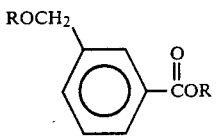

wherein R represents an alkyl group of 2 to 10 carbon atoms, which is substituted by fluorine atom(s); and ii) hydrolyzing the thus obtained alkoxymethylbenzoate represented by the formula (IV'), thereby obtaining alkoxymethylbenzoic acid represented by the formula (IV).

DETAILED DESCRIPTION OF THE INVENTION

The derivative of 1,5-diphenyl-1H-1,2,4-triazole-3-carboxamide as an active ingredient of a herbicidal composition according to the present invention, is represented by the formula (I):

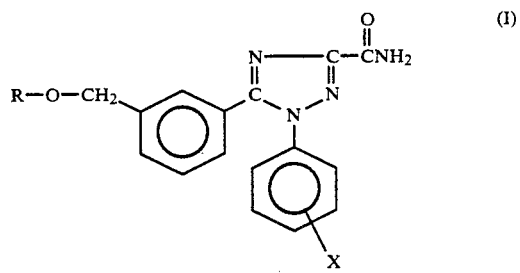

wherein R is an alkyl group of 2 to 10 carbon atoms, which is substituted by fluorine atom(s), and X is a hydrogen atom or a fluorine atom, and is obtained by reacting ammonia, in an organic solvent at a temperature of from $-10°$ to $150°$ C., with a derivative of 2-phenyl-4-phenylhydrazono-2-oxazolin-5-one represented by the formula (II):

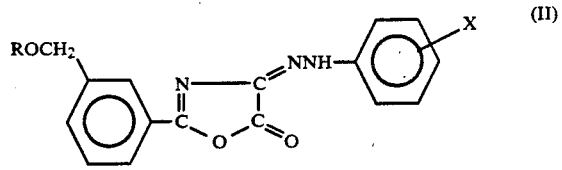

wherein R is an alkyl group of 2 to 10 carbon atoms, which is substituted by fluorine atom(s), and X is a hydrogen atom or a fluorine atom, and then reacting the thus obtained reaction mixture at a temperature of from $0°$ to $150°$ C. after making the reaction mixture acidic by adding an acid such as hydrochloric acid, acetic acid, etc. thereto.

In the formula (I), R represents an alkyl group of 2 to 10 carbon atoms, preferably an alkyl group of 3 to 6 carbon atoms, which is substituted by fluorine atom(s), preferably by 3 to 12 fluorine atoms.

The compounds represented by the formula (I) according to the present invention and the physicochemical properties thereof are exemplified in Table 1.

TABLE 1

| No. of compound | Substituent R | X | Melting point (°C.) | Nuclear magnetic resonance spectrum (60 MHz, d$_6$-DMSO, δ, ppm) |
|---|---|---|---|---|
| 1 | —CH$_2$CF$_2$CHF$_2$ | H | 170–172 | 3.82(2H, tt, 14Hz, 2Hz), 4.54(2H, s), 6.37(1H, tt, 52Hz, 6Hz), 7.15–8.0(11H, m) |
| 2 | —CH$_2$CF$_2$CHF$_2$ | 2-F | 119–121 | 3.85(2H, tt, 14Hz, 2Hz), 4.57(2H, s), 6.40(1H, tt, 52Hz, 6Hz), 7.15–8.1(10H, m) |
| 3 | —CH$_2$CF$_2$CF$_3$ | H | 156–158 | 3.80(2H, tq, 15Hz, 2Hz), 4.60(2H, s), 6.85(1H, bs), 7.0–8.0(10H, m) |
| 4 | —CH$_2$CF$_2$CHFCF$_3$ | H | 131–133 | 3.50–4.13(2H, m), 4.57(2H, s), 4.57(1H, d, 6-plet, 50Hz, 6Hz), 7.1–8.0(11H, m) |
| 5 | —CH$_2$CF$_2$CF$_2$CF$_3$ | H | 150–152 | 4.13(2H, tt, 14Hz, 2Hz), 4.67(2H, s), 7.0–8.1(11H, m) |

Since every compounds represented by the formula (I) has the selectively herbicidal activity, it can be utilized as an active ingredient of the herbicidal composition broadly used in paddy-fields and dry-field farming. Of these compounds, those of Nos. 1 to 5 are favorable and in particular, the compound No. 5 is preferable.

The compound according to the present invention, represented by the formula (I) can be produced, for instance, by the process shown by the following reaction schema (A):

REACTION SCHEMA (A)

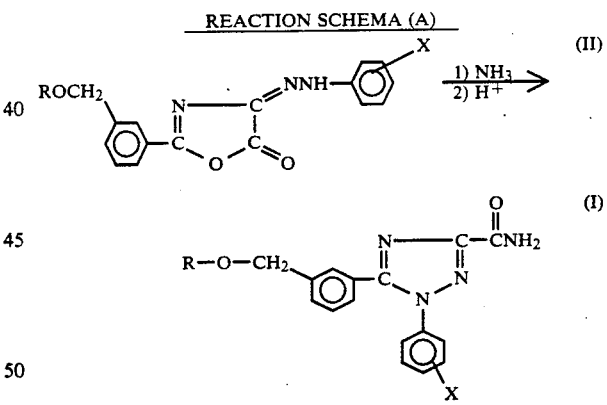

Namely, in the case of reacting ammonia with a derivative of 2-phenyl-4-phenylhydrazono-2-oxazolin-5-one represented by the formula (II) in an organic solvent, for instance, acetone, toluene, etc. for 0.1 to 20 hours at a temperature of $-10°$ to $150°$ C., then making the reaction mixture acidic by adding an acid such as hydrochloric acid, acetic acid, etc. and stirring the thus treated reaction mixture for 0.1 to 20 hours at a temperature of $0°$ to $150°$ C., thereby bringing the thus formed intermediate into dehydration and ring-closure, the compound represented by the formula (I) is obtained in a favorable yield (R and X in the formulae (I) and (II) represent the same as above).

The compound represented by the formula (II) can be synthesized, for instance, by the process shown by the following reaction schema (B):

REACTION SCHEMA (B)

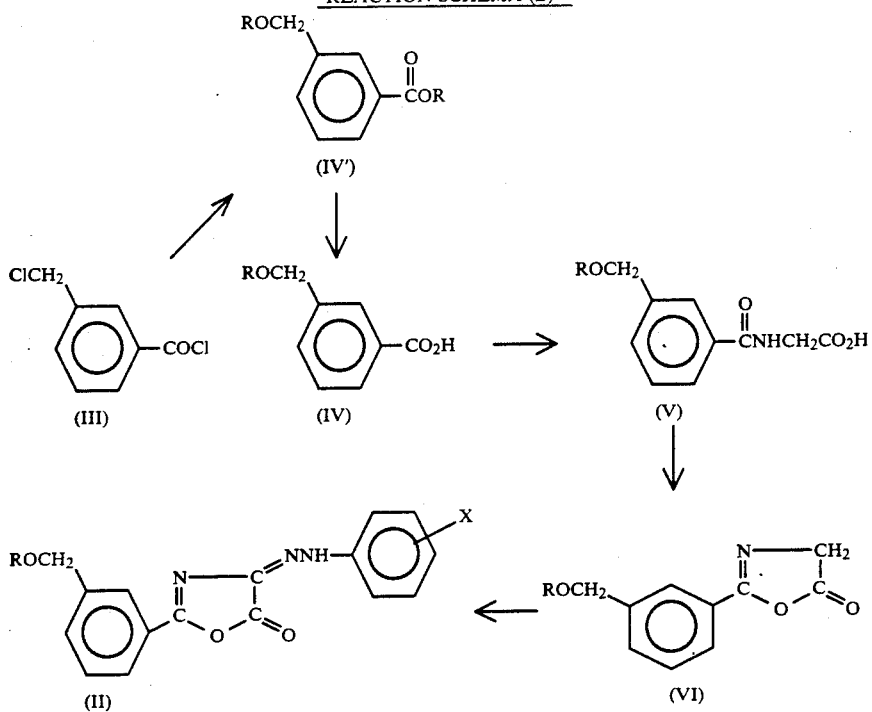

Namely, in the case of reacting 3-(chloromethyl)-benzoyl chloride (III) with not less than one equivalent of RO⊖A⊕ (wherein A represents a sodium atom or a potassium atom and R represents an alkyl group of 2 to 10 carbon atoms, which is substituted by fluorine atom(s)), in an aprotic, organic solvent for 0.1 to 30 hours at a temperature of −10° to 100° C., an alkoxymethylbenzoate represented by the formula (IV′) is obtained.

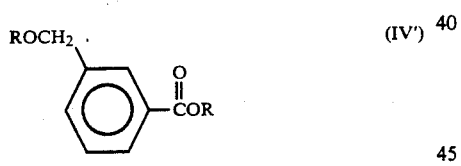

[wherein R represents an alkyl group of 2 to 10 carbon atoms, which is substituted by fluorine atom(s)]

In the case of hydrolyzing the thus obtained ester at a temperature of 0° to 100° C. without subjecting the ester to a specified purification, an alkoxymethylbenzoic acid represented by the formula (IV) is obtained.

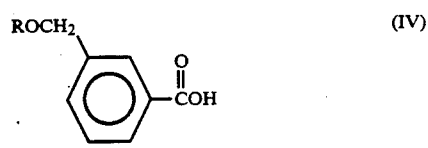

[wherein R represents an alkyl group of 2 to 10 carbon atoms, which is substituted by fluorine atom(s)]

By reacting the benzoyl chloride obtained by reacting the alkoxymethylbenzoic acid (IV) with thionyl chloride at a temperature of 0° to 100° C., with glycine in the presence of an inorganic base such as sodium hydroxide, potassium hydroxide, sodium carbonate, potassium carbonate, etc. in water or a mixed solvent of an organic solvent and water at a temperature of −10° to 15° C., preferably −5° to 5° C., an alkoxymethylhippuric acid represented by the formula (V):

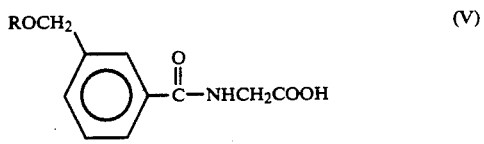

[wherein R represents an alkyl group of 2 to 10 carbon atoms, which is substituted by fluorine atom(s)] is obtained.

By reacting the thus obtained alkoxymethylhippuric acid (V) with acetic anhydride at a temperature of 30° to 100° C., a derivative of 2-phenyl-2-oxazolin-5-one represented by the formula (VI) is synthesized.

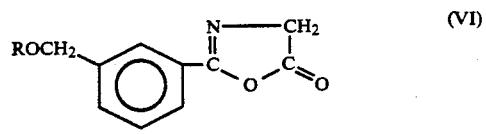

[wherein R represents an alkyl group of 2 to 10 carbon atoms, which is substituted by fluorine atom(s)]

On the other hand, by reacting a diazonium salt obtained by reacting an aniline represented by the following formula:

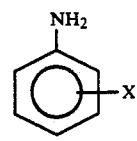

(wherein X represents a hydrogen atom or a fluorine atom) with sodium nitrite in the presence of hydrochloric acid at a temperature of −20° to 10° C., with the derivative of 2-phenyl-2-oxazolin-5-one (VI) at a temperature of not higher than 60° C., preferably −30° to 10° C., the derivative of 2-phenyl-4-phenyl-hydrazono-2-oxazolin-5-one represented by the formula (II) is obtained in a favorable yield.

The derivative of 2-phenyl-4-phenylhydrazono-2-oxazolin-b 5-one represented by the formula (II):

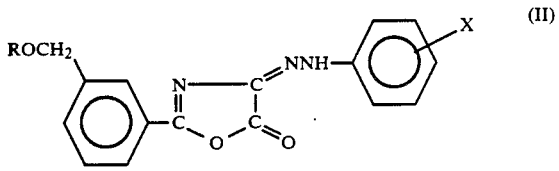

wherein R represents an alkyl group of 2 to 10 carbon atoms, which is substituted by fluorine atom(s), and X represents a hydrogen atom or a fluorine atom, alkoxymethylhippuric acid represented by the formula (V):

wherein R represents an alkyl group of 2 to 10 carbon atoms, which is substituted by fluorine atom(s), and alkoxymethylbenzoic acid represented by the formula (IV):

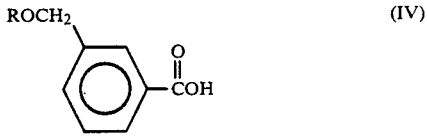

wherein R represents an alkyl group of 2 to 10 carbon atoms, which is substituted by fluorine atom(s), all of which are the intermediates of the derivative of 1,5-diphenyl-1H-1,2,4-triazole-3-carboxamide represented by the formula(I) according to the present invention and are respectively obtained by the above-mentioned methods, are the novel compounds.

The derivative of 1,5-diphenyl-1H-1,2,4-triazole-3-carboxamide according to the present invention can be used singly or as a composition such as wettable powder, emulsifiable concentrate, granule, dust, etc. in combination of a carrier (diluent) and/or an adjuvant, which has been hitherto used for the preparation of the agricultural chemicals.

The concentration of the derivative of 1,5-diphenyl-1H-1,2,4-triazole-3-carboxamide of the present invention in the above-mentioned composition is preferably from 0.1 to 50 % by weight.

The derivative of 1,5-diphenyl-1H-1,2,4-triazole-3-carboxamide according to the present invention and the herbicidal composition containing the derivative represented by the formula (I) according to the present invention as an active ingredient are applied on the soil of paddy field, farm land and/or foliage of plants so that the amount of application of the derivative represented by the formula (I) according to the present invention becomes preferably from 0.1 to 500 g/10 are.

The derivative of 1,5-diphenyl-1H-1,2,4-triazole-3-carboxamide represented by the formula (I) according to the present invention is a compound excellent in selectivity while showing an excellent herbicidal activity to wither and kill only the weeds without injuring the crops such as rice plant, wheat, corn, etc.

The present invention is explained in more detail in the following Examples; however, it should be recognized that the scope of the present invention is not restricted to these Examples.

SYNTHETIC EXAMPLE 1

Synthesis of 3-[(2,2,3,3,4,4,4-heptafluorobutoxy)methyl]benzoic acid(the compound in which R of the formula (IV) represents —CH$_2$CF$_2$CF$_2$CF$_3$)

Into a mixture of 15 ml of hexamethylphosphoroamide and 15 ml of tetrahydrofuran, 17.6 g (0.088 mol) of 2,2,3,3,4,4,4-heptafluorobutanol were dissolved, and 3.52 g (0.088 mol) of 60% NaH were added to the thus formed mixture little by little while stirring at room temperature. Into the thus obtained solution, 5.68 ml (0.040 mol) of 3-(chloromethyl)benzoyl chloride(III) were dropped at room temperature, and the thus formed mixture was stirred for 2.5 hours. Then, the reaction mixture was poured into 200 ml of iced water, and the organic matter in the mixture was extracted with ether. The solvent was distilled off from the organic layer, and 2 g of NaOH, 20 ml of water and 30 ml of ethanol were added to the residue. The thus formed mixture was heated for 2.5 hours under a reflux condenser to hydrolyze the thus formed ester. Ethanol was distilled off from the reaction mixture, and the residue was diluted with 70 ml of water and was washed with ether.

The aqueous alkaline layer was made acidic by adding a diluted hydrochloric acid and the thus separated oily matter was extracted with ether. The organic layer was washed with water and then a saturated aqueous saline solution, and the thus washed layer was dried on Na$_2$SO$_4$. By distilling ether from the thus dried ether solution, the objective product of 5.7 g was obtained as a white solid (yield : 42.7%). The melting point of the white solid was 53°–55° C.

The nuclear magnetic resonance spectrum of the thus obtained product was as follows (in CDCl$_3$,δ, ppm):

3.89(2H, tt, 14 Hz, 2 Hz); 4.62 (2H, s); 7.23~7.60(2H, m);

7.8~8.1(3H, m) and 10.53(1H, bs).

SYNTHETIC EXAMPLE 2

Synthesis of N-[3-[(2,2,3,3,4,4,4-heptafluorobutoxy)methyl]benzoyl]glycine(the compound in which R of the formula(V) represents —CH$_2$CF$_2$CF$_2$CF$_3$)

Into a mixture of 4 ml of SOCl$_2$ and 10 ml of benzene, 2.00 g (6.0 mmol) of the derivative of benzoic acid obtained in Synthetic Example 1, were added, and the thus obtained mixture was heated for 2 hours under a reflux condenser. After distilling an excess of SOCl$_2$ and benzene completely from the mixture, the residue was dissolved in 4 ml of acetonitrile.

Separately, into 12 ml of water, 0.55 g (7.3 mmol) of glycine and 0.42 g (7.5 mmol) of KOH were dissolved, and 3 ml of acetonitrile were added to the thus obtained solution.

After cooling the thus prepared mixture in an iced water bath, the thus prepared solution of acid chloride in acetonitrile and 4 ml of a separately prepared aqueous solution of 0.4 g (7.1 mmol) of KOH were added to the thus cooled solution within 3 minutes, and the thus formed mixture was stirred for 1.5 hours at room temperature.

After distilling acetonitrile off from the mixture, the residue was diluted with water, and was made acidic by adding a diluted hydrochloric acid. The educed pale-yellow matter was collected by filtration, washed with water and dried to obtain 2.04 g of the objective product of melting point of 84°~88° C. (yield : 87%).

The nuclear magnetic resonance spectrum of the thus obtained product was as follows (in $d_6$—DMSO, $\delta$, ppm):

3.94(2H, d, 6 Hz); 4.21(2H, tt, 14 Hz, 2 Hz); 4.73(2H, s);

7.0~8.1(4H, m) and 8.79(1H, t, 6 Hz).

The infrared absorption spectrum of the thus obtained product was as follows (in KBr, cm$^{-1}$):

$\nu$NH, OH; 3500~2800 and $\nu$CO; 1760~1750.

SYNTHETIC EXAMPLE 3

Synthesis of 2-[3-[(2,2,3,3,4,4,4-heptafluorobutoxy)methyl]phenyl]-4-phenylhydrazono-2-oxazolin5 -one(the compound in which R of the formula (II) represents —CH$_2$CF$_2$CF$_2$CF$_3$ and of the formula (II) represents H)

Into 6 ml of acetic anhydride, 2.00 g (5.1 mmol) of the derivative of glycine obtained in Synthetic Example 2, were added and the thus formed mixture was stirred for 10 minutes at a temperature of 60° C. to obtain a transparent solution of the azlactone (VI).

On the other hand, into a mixture of 8 ml of acetic acid and 0.9 ml of concentrated hydrochloric acid, 0.47 g (5.1 mmol) of aniline was dissolved while cooling with iced water.

A solution prepared by dissolving 0.36 g (5.2 mmol) of sodium nitrite in 1 ml of water was dropped into the thus obtained aniline solution at 0° to 3° C., and the resultant mixture was stirred for 5 minutes to prepare a solution of an aniline-diazonium salt.

Into the aforementioned azlactone solution, 0.82 g of anhydrous sodium acetate was added and after dispersing the sodium acetate well, the solution of the diazonium salt was dropped into the resultant dispersion. The thus formed mixture was stirred further for 2 hours while cooling with iced water.

Into the thus cooled mixture, water was added to educe a yellow matter, and the yellow matter was collected by filtration. By drying the thus collected yellow matter, 1.80 g of the objective product of a melting point of 138°~141° C. were obtained (yield : 84%).

The nuclear magnetic resonance spectrum of the thus obtained product was as follows (in $d_6$-DMSO, $\delta$, ppm):

4.25(2H, tt, 15 Hz, 2 Hz); 4.67(2H, s); 7.0~8.4(9H, m) and 11.62(1H, s).

The infrared absorption spectrum of the thus obtained product was as follows (in KBr, cm$^{-1}$):

$\nu$NH; 3250 and $\nu$CO; 1790.

EXAMPLE 1

Synthesis of 5-[3-[(2,2,3,3,4,4,4-heptafluorobutoxy)methylphenyl]-1-phenyl-1H-1,2,4-triazole -3-carboxamide (compound No. 5)

Into 10 ml of acetone, 1.6 g (3.3 mmol) of the derivative of hydrazone, obtained in Synthetic Example 3, were dispersed, and 0.4 ml(6.0 mmol) of concentrated ammonia was added to the thus formed dispersion at room temperature. The thus formed mixture was stirred for 30 minutes. Thereafter, 0.4 ml (4.6 mmol) of concentrated hydrochloric acid was added to the resultant mixture to make the mixture acidic, and the thus acidified mixture was stirred for 30 minutes at 50° C.

After distilling acetone off from the mixture, the residue was extracted with ethyl acetate, and the organic layer was washed with water, a saturated aqueous solution of sodium bicarbonate and a saturated aqueous solution of sodium chloride in order. By distilling the solvent off from the thus washed organic layer, crude crystals of brown in colour were obtained. By recrystallizing the crude crystals from toluene, 1.10 g of the objective product of melting point of 150°~152° C. were obtained (yield of 69%).

The infrared absorption spectrum of the thus obtained product was as follows (in KBr, cm$^{-1}$):

$\nu$NH; 3470 and $\nu$CO; 1700.

EXAMPLE 2

(Preparation of a wettable powder)

50 parts by weight of Compound No. 4, 5 parts by weight of a salt of ligninsulfonic acid, 3 parts by weight of a salt of alkylsulfonic acid and 42 parts by weight of diatomaceous earth were mixed and pulverized to prepare a wettable powder. The thus prepared wettable powder is used after diluting with water.

EXAMPLE 3

(Preparation of an emulsion)

25 parts by weight of Compound No. 3, 65 parts by weight of xylene and 10 parts by weight of polyoxyethylene alkylaryl ether were uniformly mixed together to prepare an emulsifiable concentrate. The thus prepared emulsion is used after diluting with water.

EXAMPLE 4

(Preparation of a granule)

8 parts by weight of Compound No. 5, 40 parts by weight of bentonite, 45 parts by weight of clay and 7 parts by weight of a ligninsulfonate were uniformly mixed together and the mixture was kneaded after adding water thereto. The thus kneaded mixture was processed into a granular form by an extruding granulator and was dried to obtain a granule.

In the next place, Test Examples are shown in order to show the selectively herbicidal activity of the compound according to the present invention as follows.

TEST EXAMPLE 1

Effect of the compound to the weeds in dry farm land (soil treatment before germination)

After sowing a predetermined amount of the seeds of various test plants on the soil filled in a planter (65×210×220 mm) and made to be a state of dry farm land, and covering the thus sown seeds with the soil, the wettable powder was diluted with water to a predetermined concentration and the thus formed dilution was applied uniformly on the surface of the soil by a spray gun so that the applied amount of the active ingredient becomes 100 g/10 are of the surface area of the soil. Thereafter, the thus treated seeds were grown in a green-house under control. The herbicidal effects to each weed plant and the phytotoxicity to each crop plant of the active ingredient were observed after 21 days of the treatment, and the results were evaluated according to the following standards. The thus evaluated results are shown in Table 2.

Standards for evaluation:
0 ... No herbicidal effect
1 ... Herbicidal effect of below 30%
2 ... Herbicidal effect of 31 to 50%
3 ... Herbicidal effect of 51 to 70%
4 ... Herbicidal effect of 71 to 90%
5 ... Herbicidal effect of 91 to 100%
Phytotoxicity:
—: without any phytotoxicity
±: slight phytotoxicity
+: moderate phytotoxicity
++: strong phytotoxicity
+++: severe phytotoxicity

TABLE 2

| Plant | Compound No. | | | | |
|---|---|---|---|---|---|
| | 1 | 2 | 3 | 4 | 5 |
| Amaranthus retroflexus | 5 | 5 | 5 | 5 | 5 |
| Bidens pilosa | 2 | 2 | 5 | 2 | 5 |
| Brassica arvensis | 5 | 5 | 5 | 5 | 5 |
| Stellaria media | 5 | 5 | 5 | 5 | 5 |
| Solanum nigrum | 3 | 2 | 2 | 4 | 5 |
| Abutilon theophrasti | 3 | 2 | 2 | 5 | 5 |
| Echinochloa crus-galli var. frumentacea | 2 | 1 | 1 | 4 | 5 |
| Digitaria adscendens | 2 | 2 | 2 | 2 | 5 |
| Wheat | — | — | — | — | — |
| Corn | — | — | — | — | — |

TEST EXAMPLE 2

Effect of the compound to the weeds in dry farm land (soil treatment after germination)

Following the same steps as in Test Example 1, the seeds of various plants were sown, and at the time when each plant attained to one-two leaf stage, the wettable powder was diluted with water to a predetermined concentration, and the thus formed dilution was applied uniformly onto the foliage of each plant and the surface of the soil so that the applied amount of the active ingredient becomes 100 g/10 are of the surface area of the soil. The results were evaluated as in Test Example 1 after 21 days of the treatment and are shown in Table 3.

TABLE 3

| Plant | Compound No. | | | | |
|---|---|---|---|---|---|
| | 1 | 2 | 3 | 4 | 5 |
| Amaranthus retroflexus | 5 | 5 | 5 | 5 | 5 |
| Bidens pilosa | 5 | 5 | 5 | 5 | 5 |
| Brassica arvensis | 5 | 5 | 5 | 5 | 5 |
| Stellaria media | 5 | 5 | 5 | 5 | 5 |
| Solanum nigrum | 5 | 5 | 5 | 5 | 5 |
| Abutilon theophrasti | 5 | 5 | 5 | 5 | 5 |
| Echinochloa crus-galli var. frumentacea | 2 | 2 | 2 | 2 | 2 |
| Digitaria adscendens | 2 | 2 | 2 | 3 | 2 |

TABLE 3-continued

| Plant | Compound No. | | | | |
|---|---|---|---|---|---|
| | 1 | 2 | 3 | 4 | 5 |
| Wheat | — | — | — | — | — |
| Corn | — | — | — | ± | ± |

TEST EXAMPLE 3

Effect of the compound to the weeds in paddy field and phytotoxicity to rice plant in paddy field Into a Wagner pot of 1/2000 are, to which a soil of the paddy field had been filled, water was introduced to maintain the soil in the pot at a paddy state. Onto the surface of the soil of the pot, seeds of Echinochloa crusgalli var. crusgalli, Scirpus juncoides subsp. hotarui, Alisma pygmaea, Monochoria vaginalis and Cyperus difformis were sown and into the soil in the pot, tubers of Sagittaria canaliculatum and Cyperus serotinus were planted. Furthermore, after transplanting 2 seedlings of rice plant (variety: SASANISHIKI) at two leaf-stage into the soil in the pot, the pot was kept in a green-house for 3 days. Thereafter, the dilution of the emulsion prepared as in Example 3 was uniformly applied on the surface of water in the pot so that the amount of the active ingredient becomes 100 g/10 are of the surface area of water in the pot. The herbicidal effect and the phytotoxicity to the rice seedlings of the active ingredient were investigated following the same standards as in Test Example 1 after 21 day of the treatment. The results are shown in Table 4.

TABLE 4

| Plant | Compound No. | | | | |
|---|---|---|---|---|---|
| | 1 | 2 | 3 | 4 | 5 |
| Echinochloa crus-galli | 5 | 5 | 5 | 5 | 5 |
| Scripus juncoides | 5 | 5 | 5 | 5 | 5 |
| Alisma canaliculatum | 5 | 5 | 5 | 5 | 5 |
| Monochoria vaginalis | 5 | 5 | 5 | 5 | 5 |
| Cyperus difformis | 5 | 5 | 5 | 5 | 5 |
| Sagittaria pygmaea | 5 | 5 | 5 | 5 | 5 |
| Cyperus serotinus | 4 | 4 | 4 | 5 | 5 |
| Rice seedlings | — | — | — | — | — |

What is claimed is:
1. A derivative of 1,5-diphenyl-1H-1,2,4-triazole-3-carboxamide represented by the formula (I):

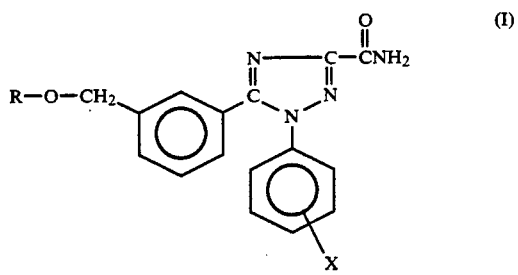

wherein R represents an alkyl group of 2 to 10 carbon atoms, which is substituted by at least one fluorine atom, and X represents a hydrogen atom or a fluorine atom.

2. A derivative according to claim 1, wherein R is —CH$_2$CF$_2$CHF$_2$, —CH$_2$CF$_2$CF$_3$, —CH$_2$CF$_2$CHFCF$_3$ or —CH$_2$CF$_2$CF$_2$CF$_3$ and X is a hydrogen atom or a fluorine atom at 2-position of the benzene ring.

3. A derivative according to claim 2, wherein R is —CH$_2$CF$_2$CF$_2$CF$_3$ and X is a hydrogen atom.

4. A herbicidal composition comprising as an active ingredient, a herbicidally effective amount of a derivative of 1,5-diphenyl-1H-1,2,4-triazole-3-carboxamide represented by the formula (I):

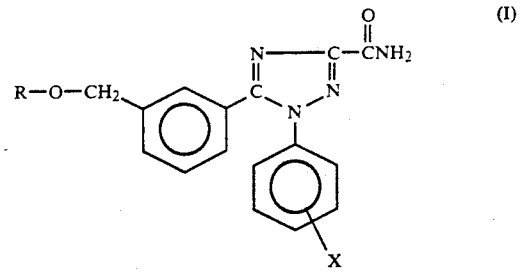

wherein R represents an alkyl group of 2 to 10 carbon atoms, which is substituted by at least one fluorine atom, and X represents a hydrogen atom or a fluorine atom, and a herbicidally acceptable carrier or adjuvant.

5. A herbicidal composition according to claim 4, wherein R is —CH$_2$CF$_2$CHF$_2$, —CH$_2$CF$_2$CF$_3$, —CH$_2$CF$_2$CHFCF$_3$ or —CH$_2$CF$_2$CF$_2$CF$_3$ and X is a hydrogen atom or a fluorine atom at 2-position of the benzene ring.

6. A herbicidal composition according to claim 5, wherein R is —CH$_2$CF$_2$CF$_2$CF$_3$ and X is a hydrogen atom.

* * * * *

UNITED STATES PATENT AND TRADEMARK OFFICE
CERTIFICATE OF CORRECTION

PATENT NO. : 5,094,684

DATED : March 10, 1992

INVENTOR(S) : SHIDA et al

It is certified that error appears in the above-identified patent and that said Letters Patent is hereby corrected as shown below:

On title page, item [54] and col. 1, lines 1-5, should read

--DERIVATIVE OF 1,5-DIPHENYL-1H-1,2,4-TRIAZOLE-3-CARBOXAMIDE,
   HERBICIDAL COMPOSITIONS CONTAINING THE DERIVATIVE AND
   PROCESS FOR PRODUCING THE DERIVATIVE--

Signed and Sealed this

Twenty-fourth Day of August, 1993

*Attest:*

BRUCE LEHMAN

*Attesting Officer*     *Commissioner of Patents and Trademarks*